United States Patent [19]

Iwasaki et al.

[11] Patent Number: 4,952,602
[45] Date of Patent: Aug. 28, 1990

[54] PHENYL BENZOTHIOPHENE HYPOLIPIDEMIC DERIVATIVES

[75] Inventors: Tameo Iwasaki, Nishinomiya; Kohki Takashima, Tokyo, both of Japan

[73] Assignee: Tanabe Seiyaku Company, Ltd., Osaka, Japan

[21] Appl. No.: 268,894

[22] Filed: Nov. 8, 1988

[30] Foreign Application Priority Data

Nov. 20, 1987 [JP] Japan .................................. 62-294736

[51] Int. Cl.$^5$ .................. C07D 409/02; C07D 333/50
[52] U.S. Cl. ..................................... 514/443; 549/44; 549/51
[58] Field of Search ...................... 549/44, 51; 514/443

[56] References Cited

FOREIGN PATENT DOCUMENTS 0188248 7/1986 European Pat. Off. .
0251315 1/1988 European Pat. Off. .

OTHER PUBLICATIONS

Vereshchagin et al., "Furylpropiolic Acids", *Chemical Abstracts*, vol. 65, col. 7123g, (1966).
Vereshchagin et al., "Some Reactions of 5-Bromo-2-Furylpropiolic Acid", *Chemical Abstracts*, vol. 63, Col. 6944b, (1965).
Iwao et al., "Generation and Diels-Adler Reation of 1-siloxy-3-Arylphthalides", *Chemistry Letters*, pp. 1263-1266, (1984).
Klemm et al., "Intramolecular Diels-Adler Cyclization into the Thiophene Ring (1)", Journal of Heterocyclic Chemistry, vol. 2, No. 3, pp. 225-227 (Sep. 1965).
Wahhab et al., "The Stobbe Condensation, Part VIII.t The Cyclisation of trans-3-Methoxycarbonyl . . . ", *Journal of Chemistry Soc.* (C), (19), pp. 3171-3173, (1971).
Wahhab et al., "The Stobbe Condensation. Part V.t The Cyclisation of 3-Methoxycarbonyl-cis-4-(2-furyl) . . . ", Journal of Chemistry Soc. (C), (7), pp. 867-869, (1968).
Wahhab et al., "The Stobbe Condensation, Part IX (1). The Cyclisation of (E)-3-Methoxycarbonyl-4- . . . ",
*Journal fur praktische Chemie,* vol. 313, pp. 247-253 (1971).
Guirguis et al., "Synthesis of Enol Lactones of 3-Aroyl-1-2(thienylmethylene)-propionic Acids . . . ", *Liebigs Ann. Chem.,* (6), pp. 1003-1011, (1986).
Moussa, et al., "Synthesis and Biological Screening . . . Part III", Indian J. Chem., Sect. B, 15B (6), 555-7, 1977.
El-Rayyes, et al., "Stobbe Condensation . . .", J. Prakt. Chem. 317 (4), 552-60, 1975.
Moussa, et al., "Heteropolycyclic Molecules Part IX", J. Heterocycl. Chem. 18 (8) 1519-22, 1981.

*Primary Examiner*—Mary C. Lee
*Assistant Examiner*—Catherine Scalzo
*Attorney, Agent, or Firm*—Browdy & Neimark

[57] ABSTRACT

Biphenyl derivative of the formula:

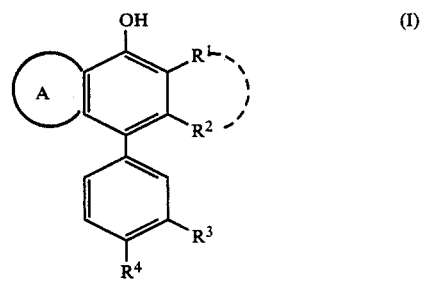

wherein $R^1$ is hydrogen atom or a lower alkoxycarbonyl group and $R^2$ is a lower alkoxycarbonyl group, or $R^1$ and $R^2$ are combined together to form a group of the formula: each of $R^3$ and $R^4$ is a lower alkoxy group; and Ring A is a substituted or unsubstituted sulfur-containing or nitrogen-containing heterocyclic ring, with the claims being drawn to Ring A as thiophene and a pharmaceutically acceptable salt thereof are disclosed. Said biphenyl derivative (I) and its salt have excellent hypolipidemic activity and are useful for treatment or prophylaxis of hyperlipidemia and/or arteriosclerosis.

7 Claims, No Drawings

PHENYL BENZOTHIOPHENE HYPOLIPIDEMIC DERIVATIVES

This invention relates to biphenyl derivatives useful as hypolipidemic agents.

Hyperlipidemia such as hypercholesterolemia has been known to be a major risk factor for arteriosclerosis including atherosclerosis, and drugs such as clofibrate [chemical name: 2-(4-chlorophenoxy)-2-methylpropanoic acid ethyl ester], probucol [chemical name: 4,4'-[(1-methylethylidene)bis(thio)]bis[2,6-bis(1,1-dimethylethyl)phenol]] and cholestyramine resin have been used as hypoliopidemic agents.

It is known that cholesterol in blood serum exists in various forms such as very-low-density lipoprotein (VLDL) cholesterol, low-density lipoprotein (LDL) cholesterol and high-density lipoprotein (HDL) cholesterol. In this connection, it is also known that HDL has a therapeutic or prophylactic effect for arteriosclerosis because of its preventing effect on deposition of cholesterol on the arterial wall, while VLDL and LDL induce the deposition of cholesterol and are causative of arteriosclerosis [Annals of Internal Medicine, vol. 90, page 85-91 (1979)].

Therefore, in the field of therapy or prophylaxis of arteriosclerosis, it has been desired to develop a hypolipidemic agent which can decrease the serum total cholesterol level and at the same time can increase the serum HDL-cholesterol level.

As a result of various investigations, we have now found that a biphenyl derivative of the formula:

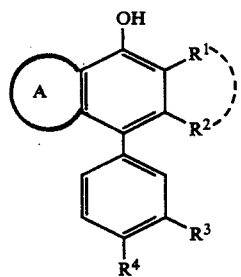

(I)

wherein $R^1$ is hydrogen atom or a lower alkoxycarbonyl group and $R^2$ is a lower alkoxycarbonyl group, or $R^1$ and $R^2$ are combined together to form a group of the formula:

each of $R^3$ or $R^4$ is a lower alkoxy group; and Ring A is a substituted or unsubstituted sulfur-containing or nitrogen-containing heterocyclic ring.

Thus, an object of the present invention is to provide a novel biphenyl derivative (I) which is useful for therapeutic treatment or prophylaxis of hyperlipidemia and/or arteriosclerosis. Another object is to provide a novel pharmaceutical composition for use as a hypolipidemic agent, which comprises the biphenyl derivative (I) as the therapeutically active ingredient. The other object is to provide processes for preparing said novel biphenyl derivative. Further object is to provide an intermediate for the preparation of the biphenyl derivative (I).

The biphenyl derivative (I) or a pharmaceutically acceptable salt thereof shows a potent hypolipidemic activity and is particularly characterized in that it can increase the serum HDL-cholesterol level while decreasing the serum total cholesterol level. For example, when the effect of a test compound (dose: 100 mg % in diet) on the serum total cholesterol level and the serum HDL-cholesterol level was examined by feeding rats with a diet supplemented with cholesterol and sodium cholate, 4-hydroxy-5,6-bis(methoxycarbonyl)-7-(3,4-dimethoxyphenyl)benzo[b]thiophene of the present invention showed 51% decrease in serum total cholesterol level and 88% increase in serum HDL-cholesterol level.

Moreover, the biphenyl derivative (I) and a pharmaceutically acceptable salt thereof are low in toxicity and substantially free from undesirable side effects such as hepatic dysfunction. For example, when the above-mentioned compound of the present invention was administered orally to mice at a dose of 1000 mg/kg, no mice died even 5 days after the oral administration.

Representative examples of the biphenyl derivative of the present invention include those of the formula (I) in which $R^1$ is hydrogen atom, or a lower alkoxycarbonyl group (e.g., methoxycarbonyl group, ethoxycarbonyl group) and $R^2$ is a lower alkoxycarbonyl group (e.g., methoxycarbonyl group, ethoxycarbonyl group), or $R^1$ and $R^2$ are combined together to form a group of the formula:

each of $R^3$ and $R^4$ is a lower alkoxy group (e.g., methoxy group, ethoxy group); and Ring A is a substituted or unsubstituted sulfur-containing or nitrogen-containing heterocyclic ring (e.g., thiophene ring, pyrrole ring, imidazole ring, pyridine ring, indole ring, quinoline ring, thiazole ring, oxazole ring), and examples of the substituent on a sulfur-containing or nitrogen-containing heterocyclic ring include a phenylsulfonyl group and a phenylsulfonyl group substituted with a lower alkyl group (e.g., toluenesulfonyl group). Among these derivatives, prefered examples include those of the formula (I) in which $R^1$ is hydrogen atom or an alkoxycarbonyl group of 2 to 5 carbon atoms and $R^2$ is an alkoxycarbonyl group of 2 to 5 carbon atoms, or $R^1$ and $R^2$ are combined together to form a group of the formula:

each of $R^3$ and $R^4$ is an alkoxy group of one to 4 carbon atom(s); and Ring A is thiophene ring, pyridine ring, indole ring or N-phenylsulfonylindole ring.

According to the present invention, the biphenyl derivatives of formula (I) in which $R^1$ is hydrogen atom or a lower alkoxycarbonyl group and $R^2$ is a lower alkoxycarbonyl group, can be prepared by reacting an acetylene compound of the formula:

 (II)

wherein $R^{11}$ is hydrogen atom or a lower alkoxycarbonyl group; and $R^{21}$ is a lower alkoxycarbonyl group, with a compound of the formula:

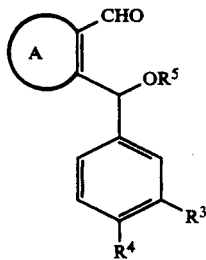 (III)

or

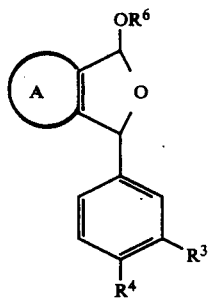 (IV)

wherein $R^5$ is hydrogen atom, an alkyl group or an acyl group; $R^6$ is a lower alkyl group; and $R^3$, $R^4$ and Ring A are the same as defined above, or a di-lower alkyl acetal thereof.

On the other hand, the biphenyl derivative of the formula (I) in which $R^1$ and $R^2$ are combined together to form a group of the formula:

can be prepared by reductive lactonization of a bis-lower alkoxycarbonyl-biphenyl compound of the formula:

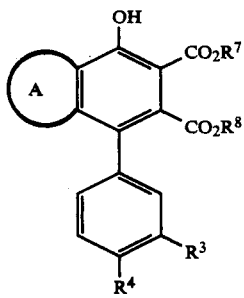 (I-a)

wherein each of $R^7$ and $R^8$ is a lower alkyl group; and $R^3$, $R^4$ and Ring A are the same as defined above.

Each of the above-mentioned starting compound may be used as a salt thereof. Examples of the salt of the starting compounds (III) (and the di-lower alkyl acetal thereof), (IV) and (I-a) in which Ring A is a nitrogen-containing heterocyclic ring, include an organic or inorganic acid-addition salt and the like. Examples of the salts of starting compound (III) (and the di-lower alkyl acetal thereof) in which $R^5$ is hydrogen atom and the compound (I-a) include an alkali metal salt, alkaline earth metal salt, quarternary ammonium salt and the like.

The reaction of the acetylene compound (II) with the aldehyde compound (III), its di-lower alkyl acetal or a salt thereof, may be accomplished in the presence of an acid in or without a solvent. Examples of the acid include inorganic acid (e.g., sulfuric acid) and organic acid (e.g., trifluoroacetic acid, acetic acid, formic acid, methanesulfonic acid, p-toluenesulfonic acid). Benzene, toluene, xylene, tetrahydrofuran, dimethoxyethane, dioxane and the like may be preferably used as the solvent. The reaction proceeds between the temperature of ice-cooling and the boiling point of the solvent.

The reaction of the acetylene compound (II) with the dihydrofuran compound (IV) or a salt thereof, may be accomplished in the presence of an acid or a base in or without a solvent. Examples of the base include alkali metal alkoxide, alkali metal di-lower alkylamide and the like, and the acid and the solvent used in the reaction of the acetylene compound (II) with the aldehyde compound (III) or its di-lower alkyl acetal may also be preferably used in the reaction. The reaction smoothly proceeds between the temperature of ice-cooling and the boiling point of the solvent.

On the other hand, the reductive lactonization of the bis-lower alkoxycarbonyl-biphenyl compound (I-a) or a salt thereof may be accomplished by reducing said compound with a conventional reducing agent in a solvent followed by treating the thus-obtained product with an acid. Examples of the reducing agent include borane complex, sodium borohydride-boron trifluoride etherate complex, calcium borohydride, lithium borohydride, lithium aluminum hydride and the like. Tetrahydrofuran, dioxane and the like may be preferably used as the solvent. The organic or inorganic acids which are used in the reaction of acetylene compound (II) or its di-lower alkyl acetal may be preferably used for the successive induced lactonization of the reduction product. Examples of the solvent used in the induced lactonization include a lower alkanol, tetrahydrofuran, ethyl acetate, dioxane and the like. Each step of the above-mentioned reductive lactonization may be preferably carried out at room temperature or under heating.

Further, the biphenyl derivative of the formula (I) in which Ring A is an unsubstituted nitrogen-containing heterocyclic ring may be obtained according to a conventional manner by removing the substituent on the nitrogen atom of the biphenyl derivative (I) in which Ring A is an N-substituted nitrogen-containing heterocyclic ring. For example, when Ring A is N-phenylsulfonylindole ring, said N-substituent may be removed according to a conventional reduction method (e.g., cathodic reduction).

The biphenyl derivative (I) may be used, for the purpose of the present invention, either in the free form or in the form of a pharmaceutically acceptable salt. Examples of the pharmaceutically acceptable salt of the biphenyl derivative (I) include alkali metal salts (e.g., sodium salt, potassium salt), alkaline earth metal salts (e.g., calcium salt), quarternary ammonium salts (e.g., tetramethylammonium salt, tetraethylammonium salt) and so forth. Further, the biphenyl derivative of the formula (I) in which Ring A is a nitrogen-containing heterocyclic ring, may be used as an inorganic acid-addition salt (e.g., hydrochloride, hydrobromide, sulfate), organic acid-addition salt (e.g., acetate, oxalate, benzenesulfonate) and the like.

The biphenyl derivative (I) or a pharmaceutically acceptable salt thereof may be administered either orally or parenterally to warm-blooded animals including human beings, while it is generally preferred to administer it through oral route. The biphenyl derivative (I) or a salt thereof may be used in the form of a pharmaceutical composition in admixture with a pharmaceutically acceptable adjuvant or carrier therefor. For example, the pharmaceutical composition for oral administration may be in a solid dosage form such as tablets, pills, powders, capsules or granules; and it may contain a pharmaceutically acceptable adjuvant or carrier such as calcium carbonate, calcium phosphate, corn starch, potato starch, sugar, lactose, talcum, magnesium stearate and the like. Said pharmaceutical composition in a solid form may further contain binders, diluents, disintegrants, wetting agents and so forth. Alternatively, the pharmaceutical composition for oral administration may be in a liquid dosage form such as aqueous or oily suspensions, solutions, syrup, elixirs and the like. Suitable adjuvants for such liquid dosage form may include liquid vehicles, suspending agents, surfactants, non-liquid vehicles and so forth. On the other hand, the pharmaceutical composition for parenteral administration may be in the form of injections or suppositories. The injections may be either a solution or a suspension, which may contain a pharmaceutically acceptable carrier such as essential oil (e.g., peanut oil, corn oil) or aprotic solvent (e.g., polyethyleneglycol, polypropyleneglycol, lanolin, coconut oil).

As mentioned hereinbefore, the biphenyl derivative (I) and a pharmaceutically acceptable salt thereof have a potent hypolipidemic activity. Especially, the biphenyl derivative (I) and a salt thereof are characterized in that they can decrease serum total cholesterol level and at the same time can increase the serum HDL-cholesterol level in blood. Therefore, the biphenyl derivative (I) and a salt thereof are useful for the treatment or prophylaxis of hyperlipidemia (e.g., hypercholesterolemia) or arteriosclerosis (e.g., atherosclerosis, Moenkeberg's sclerosis, arteriolosclerosis) in warm-blooded animals including human beings.

The daily dose of the biphenyl derivative (I) or a pharmaceutically acceptable salt thereof may vary over a wide range depending on the severity of the diseases; the ages, weight and condition of patient and the like, but the preferred daily dose may be usually in the range of 1.5 to 35 mg, especially 5 to 25 mg, per kg of body weight.

Concomitantly, both of the starting compounds (III) and (IV) are novel, and the starting compound (III) or a di-lower alkyl acetal thereof, can be prepared by reacting an acetal compound of the formula:

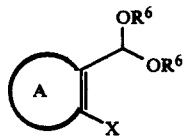

wherein X is hydrogen or bromine atom; and $R^6$ and Ring A are the same as defined above, with a substituted benzaldehyde of the formula:

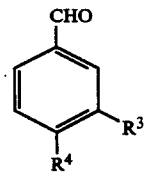

wherein $R^3$ and $R^4$ are the same as defined above, in the presence of an alkyl lithium to give the compound (III) in which $R^5$ is hydrogen atom, and, if required, hydrolyzing acetal group and/or alkylating or acylating the hydroxy group of the product.

Meanwhile, the starting compound (III) in which $R^5$ is a lower alkyl group may be prepared by alkylating a compound of the formula:

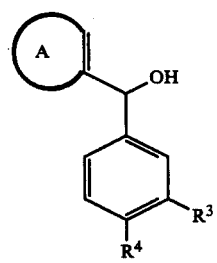

wherein $R^3$, $R^4$ and Ring A are the same as defined above, according to a conventional method, and reacting the resulting product with dimethylformamide in the presence of an alkyl lithium.

Moreover, the dihydrofuran compound (IV) may be obtained by heating the di-alkyl acetal of the aldehyde compound (III) ($R^5$=hydrogen atom) with boric acid or acetic acid in a solvent.

EXPERIMENT (Effect on serum total cholesterol level and serum HDL-cholesterol level)

Male SD rats (body weight: 110 to 170 g, one group consisting of 5 or 6 rats) were fed ad libitum for 4 days with a diet containing 2 w/w % of cholesterol and 0.5 w/w % of sodium cholate. Then, the rats were further fed ad libitum with the same diet containing 100 mg % of a test compound. The control group of the rats were fed with the diet not containing the test compound. Three days later, the rats were anesthetized with ether. After the body weight of the rats were measured, blood was collected from abdominal aorta thereof. The blood was allowed to stand at room temperature for one hour and centrifuged. Then, the total cholesterol level in the serum thus obtained was measured enzymatically according to the method described in Clinical Chemistry, vol. 20, page 470 (1974). On the other hand, HDL-cholesterol in the above-obtained serum was obtained as soluble fraction after precipitating VLDL- and LDL-cholesterol using dextran sulfate [Canadian Journal of Biochemistry, vol. 47, page 1043 (1969)], and then serum HDL-cholesterol level was measured enzymatically according to the above-mentioned method. On the basis of the results obtained above, the effects of the test compound on the serum total cholesterol level and serum HDL-cholesterol level were estimated according to the formulae:

PERCENTAGE DECREASE IN SERUM TOTAL CHOLESTEROL LEVEL =

$$\left[1 - \frac{\text{Average value of serum total cholesterol level in the medicated group of rats}}{\text{Average value of serum total cholesterol level* in the control group of rats}}\right] \times 100$$

PERCENTAGE INCREASE IN SERUM HDL-CHOLESTEROL LEVEL =

$$\left[\frac{\text{Average value of serum HDL-cholesterol level in the medicated group of rats}}{\text{Average value of serum HDL-cholesterol level** in the control group of rats}} - 1\right] \times 100$$

Note:
*Average value of serum total cholesterol level in the control group was 152 to 230 mg/dl.
**Average value of serum HDL-cholesterol level in the control group was 13.6 to 27.6 mg/dl.

Results are shown in the following Table.

TABLE 1

| Compound (I) | | | Decrease of Serum Total Cholesterol (%) | Increase of HDL-Cholesterol (%) |
|---|---|---|---|---|
| Ring A | $R^1/R^2$ | $R^3/R^4$ | | |
| thiophene | —CO$_2$Me respectively | —OMe respectively | 51 | 88 |
| thiophene | —CO$_2$Et respectively | —OMe respectively | 46 | 42 |
| N-phenylsulfonyl indole | —CO$_2$Et respectively | —OMe respectively | 25 | 28 |
| thiophene | | —OMe respectively (with cyclic carbonate group) | 35 | 39 |
| N-phenylsulfonyl indole | " | —OMe respectively | 20 | 74 |

Further, immediately after the collection of blood in the above-mentioned experiment, the liver of each rat was taken out, and the weight thereof was measured. Then, the relative liver weight was examined according to the following formula, and the average relative liver weight was compared with that of the control group. The test compounds used in the above-mentioned experiments caused no substantial increase in the relative liver weight.

$$\text{RELATIVE LIVER WEIGHT} = \frac{\text{Liver weight}}{\text{Body weight}} \times 100$$

EXAMPLE 1

29 mg of trifluoroacetic acid are added to a solution of 1.5 g of 2-(α-acetoxy-3,4-dimethoxybenzyl)-3-thiophenecarboaldehyde and 1.8 g of acethylene dicarboxylic acid dimethyl ester in 2.5 ml of benzene, and the mixture is refluxed for one hour. After cooling, the mixture is evaporated under reduced pressure to remove the solvent. The residue is purified by silica gel column chromatography [solvent:hexane-ethyl acetate (1:1)], and the eluate is evaporated under reduced pressure to remove the solvent, whereby 350 mg of 4-hydroxy-5,6-bis(methoxycarbonyl)-7-(3,4-dimethoxyphenyl)benzo[b]thiophene are obtained as colorless crystals.

The product is recrystallized from a mixture of hexane and ethyl acetate to give colorless prisms.
M.p. 147° to 148° C.
NMR (CDCl$_3$)δ: 3.62(S, 3H), 3.86(S, 3H), 3.93(S, 6H), 6.94(S, 3H), 7.38(d, J=6 Hz, 1H), 7.65(d, J=6 Hz, 1H), 11.73(S, 1H)
Mass(m/z): 402(M$^+$)

EXAMPLE 2 TO 5

The corresponding starting compounds are reacted in the same manner as described in Example 1, whereby the compounds listed in Table 2 are obtained. (In the following Tables, Me and Et represent methyl and ethyl group, respectively.)

TABLE 2

(I-α)

[Structure: Ring A fused to benzene ring with OH, $R^{11}$, $R^{21}$ substituents, attached to phenyl ring with $R^3$, $R^4$]

| Example Nos. | Compound (I-α) $R^1/R^2$ | $R^3/R^4$ | Ring A | Physical properties |
|---|---|---|---|---|
| 2 | —CO₂Me | —OMe | [thiophene ring S] | M.p. 188° C. |
| 3 | " | —OEt | [thiophene ring S] | M.p. 129–130° C. |
| 4 | —CO₂Et | —OMe | " | M.p. 119–120° C. |
| 5 | " | —OEt | " | M.p. 87–88° C. |

EXAMPLE 6

45 ml of 1.55M n-butyl lithium in hexane are added at a temperature of −70° to −50° C. to a solution of 7.0 g of diisopropylamine in 100 ml of tetrahydrofuran. The mixture is stirred for 30 minutes at a temperature of 0° to 10° C., and then chilled to −70° C. Further, a solution of 5.0 g of 3-(3,4-dimethoxyphenyl)-1-methoxy-1H,3H-pyridino[2,3-c]furan in 20 ml of tetrahydrofuran is added thereto for 10 minutes, and the mixture is stirred at the same temperature for 10 minutes. A solution of 4.2 g of acetic acid and 2.7 g of acetylenedicarboxylic acid dimethyl ester in 20 ml of tetrahydrofuran are added further thereto. The mixture is stirred at the same temperature for 10 minutes. A solution of 4.2 g of acetic acid in 10 ml tetrahydrofuran is added to the mixture at room temperature, and the mixture is stirred for 10 minutes. The reaction mixture is poured into 300 ml of water and extracted with ethyl acetate. The extract is dried and evaporated to remove the solvent. The residue is purified by silica gel column chromatography [solvent: hexane-ethyl acetate (1:2)], and the eluate is evaporated under reduced pressure to remove the solvent, whereby 1.8 g of pale brown oil are obtained. Said oil is dissolved in benzene, and 1.6 g of trifluoroacetic acid are added to the solution. The mixture is stirred at room temperature for one hour, and evaporated under reduced pressure to remove the solvent. 100 ml of ethyl acetate is added to the residue, and the mixture is neutralized with 100 ml of aqueous saturated sodium bicarbonate solution. The organic layer is dried and evaporated under reduced pressure to remove the solvent. The resulting pale brown crystals are washed with ether to give 1.3 g of 5-hydroxy-6,7-bis(methoxycarbonyl)-8-(3,4-dimethoxyphenyl)quinoline.

The product is recrystallized from a mixture of ethyl acetate and hexane to give pale brown needles.

M.p. 183° to 184° C.

NMR (CDCl₃)δ: 3.56 (S, 3H) 3.83(S, 3H), 3.90(S, 3H), 3.94(S, 3H), 6.88(S, 3H), 7.42(dd, J=9 Hz, 5 Hz, 1H), 8.73(dd, J=9 Hz, 2 Hz, 1H), 8.96(dd, J=5 Hz, 2 Hz, 1H), 12.31(S, 1H)

Mass (m/z): 397(M⁺)

EXAMPLE 7

A solution of 31.4 g of 3-(3,4-dimethoxyphenyl)-1-methoxy-4-phenylsulfonyl-1H,3H-indolo[2,3-c]furan and 28.5 g of acetylene dicarboxylic acid dimethyl ester in 400 ml of benzene is refluxed for 30 minutes. 127 mg of p-toluenesulfonic acid monohydrate is added to the solution, and the mixture is further refluxed for one hour. After cooling, the mixture is evaporated to remove the solvent, and 400 ml of ether is added to the residue. Crystalline precipitates are collected by filtration, whereby 27.5 g of 4-hydroxy-2,3-bis-(methoxycarbonyl)-1-(3,4-dimethoxyphenyl)-9-phenylsulfonylcarbazole are obtained.

M.p. 192° to 193° C.

NMR (CDCl₃)δ: 3.80 (S, 3H) 3.86 (S, 3H), 5.27 (S, 2H), 6.60 to 8.33 (m, 12H), 9.90 to 10.16 (m, 1H)

Mass (m/z): 515(M⁺)

EXAMPLE 8

The corresponding strating compounds are reacted in the same manner as described in Example 7, whereby 4-hydroxy-2,3-bis(ethoxycarbonyl)-1-(3,4-dimethoxyphenyl)-9-phenylsulfonylcarbazole is obtained.

M.p. 202° to 203° C.

EXAMPLE 9

0.24 ml of borane-methylsulfide complex is added to a solution of 5.0 g of 4-hydroxy-5,6-bis(methoxycarbonyl)-7-(3,4-dimethoxyphenyl)benzo[b]thiophene in 50 ml of tetrahydrofuran. The mixture is refluxed for 40 minutes, and then 80 ml of methanol and one drop of trifluoroacetic acid are added thereto. The mixture is further refluxed for 2.5 hours. After cooling, the reaction mixture is evaporated under reduced pressure, and the residue is washed with methanol, whereby 3.95 g of 4-hydroxy-5-hydroxymethyl-7-(3,4-dimethoxyphenyl)-benzo[b']thiophene-6-carboxylic acid lactone are obtained as pale yellow amorphous.

The product is recrystallized from a mixture of ethyl acetate and tetrahydrofuran to give yellow green amorphous.

M.p. 223° to 224° C. (decomp.)

NMR (CDCl₃)δ: 3.86 (S, 3H) 3.93 (S, 3H), 5.32 (S, 2H), 6.90 to 7.20 (m, 3H), 7.53 (d, 1H), 7.71 (d, 1H), 9.96 (br, 1H)

Mass (m/z): 342(M⁺)

EXAMPLES 10 AND 11

The corresponding starting compounds are treated in the same manner as described in Example 9, whereby the compounds listed in Table 3 are obtained.

TABLE 3

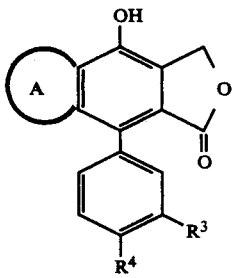

(I-β)

| Example Nos. | Compound (I-β) Ring A | R³/R⁴ | Physical properties |
|---|---|---|---|
| 10 | (thiophene with methyl) | —OEt | M.p. 223–224° C. (decomp.) |
| 11 | (indole with N-SO₂-phenyl, methyl) | —OMe | M.p. 192–193° C. |

EXAMPLE 12

A solution of 4.0 g of 4-hydroxy-2,3-bis(methoxycarbonyl)-1-(3,4-dimethoxyphenyl)-9-phenylsulfonylcarbazole in 50 ml of N,N-dimethylformamide and 4.2 g of tetraethylammonium toluenesulfonate are put in the cathodic compartment equipped with a mercury pool cathode. 10 ml of N,N-dimethylformamide and 4.2 g of tetraethylammonium toluenesulfonate are put in the anodic compartment equipped with a graphite anode. A constant current of 200 mA is passed through the solution under ice-cooling and is stopped when the amount of electricity reached to 1351 coulomb. The catholyte is taken out by using 50 ml of methanol, and 0.9 ml of acetic acid is added thereto. The solution is evaporated under reduced pressure to remove the solvent, and the residue is added to an aqueous saturated sodium bicarbonate solution. The resulting crystals are obtained by filtration and washed with water, whereby 2.2 g of 4-hydroxy-2,3-bis(methoxycarbonyl)-1-(3,4-dimethoxyphenyl)carbazole are obtained.

The product is recrystallized from a mixture of methanol and tetrahydrofuran to give colorless prisms.

M.p. 252° to 253° C. (decomp.)

NMR (CDCl₃)δ: 3.71(S, 3H) 3.95(S, 3H), 4.00(S, 6H), 6.93 to 8.35(m, 8H), 10.80 to 12.03(m, 1H)

Mass (m/z): 435(M+)

EXAMPLES 13 AND 14

The corresponding starting compounds are treated in the same manner as described in Example 12, whereby the compounds listed in the Table 4 are obtained.

TABLE 4

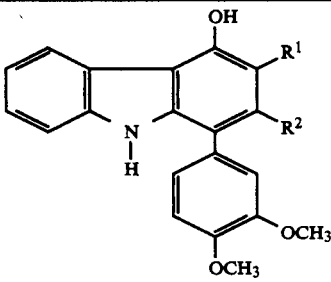

(I-γ)

| Example Nos. | Compound (I-γ) R¹/R² | Physical properties |
|---|---|---|
| 13 | —CO₂Et respectively | M.p. 249–250° C. |
| 14 | (–OCH₂O–) | M.p. 290–291° C. (decomp.) |

REFERENCE EXAMPLE 1

(1) 32.6 ml of 1.55M n-butyl lithium in hexane are added to a solution of 11.6 g of 2-bromo-3-dimethoxymethylpyridine in tetrahydrofuran. Said addition is carried out under stirring with cooling. After stirring the mixture under cooling, a solution of 8.3 g of 3,4-dimethoxybenzaldehyde in tetrahydrofuran is added thereto. The mixture is stirred, and then poured into water. Ethyl acetate is further added thereto, and organic layer is separated. Said organic layer is washed, dried and evaporated to remove the solvent. The residue is purified by using silica gel column, whereby 8.4 g of 2-(α-hydroxy-3,4-methoxybenzyl)-3-dimethoxymethylpyridine are obtained as yellow crystals.

M.p. 91° to 92° C. (recrystallized from a mixture of ethyl acetate and hexane)

(2) 11 g of the product obtained in the paragraph (1) is dissolved in toluene with heating, and 32 g of boric acid are added thereto. After cooling the mixture, it is evaporated to remove the solvent. Ethyl acetate is added to the residue, and the mixture is washed with water, dried and evaporated under reduced pressure to remove the solvent. The residue is purified by using silica gel column, whereby 6.5 g of 3-(3,4-dimethoxyphenyl)-1-methoxy-1H,3H-pyridino[2,3-c]furan are obtained as pale brown syrup.

REFERENCE EXAMPLE 2

(1) 10.0 g of 3-dimethoxymethylthiophene are reacted in the same manner as described in Reference example 1-(1), whereby 18 g of 2-(α-hydroxy-3,4-dimethoxybenzyl)-3-dimethoxymethylthiophene are obtained as syrup.

(2) 1.9 g of boric acid are added to a solution of 1.0 g of the product obtained in the paragraph (1) in toluene, and the mixture is refluxed. After cooling, the mixture is evaporated under reduced pressure to remove the solvent. Ethyl acetate is added to the residue, and the mixture is washed, dried and evaporated under reduced pressure to remove the solvent. The residue is purified by using silica gel column, whereby 470 mg of 2-(α-hydroxy-3,4-dimethoxybenzyl)-3-thiophenecarboaldehyde are obtained as colorless crystals.

(3) A solution of 818 mg of triethylamine in tetrahydrofuran is added under ice-cooling to a tetrahydrofuran solution of 1.5 g of the product obtained in the paragraph (2), 661 mg of acetic anhydride, and 20 mg of N,N-dimethylaminopyridine and the mixture is stirred. Methanol is added to the reaction mixture, and the mixture is evaporated under reduced pressure to remove the solvent. Ethyl acetate is added to the residue, and the mixture is washed with an aqueous saturated sodium bicarbonate solution, dried and evaporated under reduced pressure to remove the solvent. The residue is purified by using silica gel column, whereby 1.7 g of 2-(α-acetoxy-3,4-dimethoxybenzyl)-3-thiophenecarboaldehyde are obtained as colorless crystals.

M.p. 91° to 92° C. (recrystallized from a mixture of ethyl acetate and hexane)

REFERENCE EXAMPLE 3

The corresponding starting compounds are reacted in the same manner as described in Reference example 2, whereby 2-(α-acetoxy-3,4-diethoxybenzyl)-3-thiophenecarboaldehyde is obtained.

M.p. 68° C.

REFERENCE EXAMPLE 4

(1) 40 ml of 1.55M n-butyl lithium in hexane are added under stirring with cooling to a tetrahydrofuran solution of 19 g of 1-phenylsulfonyl-3-dimethoxymethylindole and 6.5 g of N,N,N',N'-tetramethylethylenediamine. The mixture is stirred at room temperature, and then a solution of 9.3 g of 3,4-dimethoxybenzaldehyde in tetrahydrofuran is added thereto under cooling. The mixture is further stirred at room temperature, poured into water, and then extracted with ethyl acetate. The extract is dried and evaporated under reduced pressure to remove the solvent. The residue is purified by using silica gel column. 17 g of 1-phenylsulfonyl-2-(α-hydroxy-3,4-dimethoxybenzyl)-3-dimethoxymethylindole are obtained as syrup.

IR$\nu_{Max}^{Nujol}$ (cm$^{-1}$): 3450

(2) 0.6 g of boric acid is added to a toluene solution of 0.5 g of the product obtained in the paragraph (1), and the mixture is refluxed. After cooling, the mixture is evaporated to remove the solvent. Ethyl acetate is added to the residue, and the mixture is washed with water, dried and evaporated to remove the solvent. The residue is purified by using silica gel column, whereby 370 mg of 3-(3,4-dimethoxyphenyl)-1-methoxy-4-phenylsulfonyl-1H,3H-indolo[2,3-c]furan are obtained as pale yellow crystals.

M.p. 131° to 132° C.

REFERENCE EXAMPLE 5

(1) 24 ml of 2.5M n-butyl lithium in hexane are added dropwise to a tetrahydrofuran solution of 10.85 g 4-bromoveratrole under cooling. After stirring the mixture, 5.61 g of 3-thiophenecarboaldehyde are added thereto, and warmed up to room temperature. Water is added thereto, and the mixture is extracted with ethyl acetate. The extract is dried and evaporated under reduced pressure to remove the solvent, whereby 3-(α-hydroxy-3,4-dimethoxybenzyl)thiophene is obtained. 2.8 g of sodium hydride are added to a solution of the product in dimethylformamide, and the mixture is stirred at room temperature. 4.7 ml of methyl iodide are added thereto, and the mixture is stirred. A small amount of water is added thereto, and the mixture is evaporated under reduced pressure to remove the solvent. Water is added to the residue and the mixture is extracted with ethyl acetate. The extract is dried and evaporated under reduced pressure to remove the solvent. The residue is purified by using silica gel column, whereby 10.5 g of 3-(α-methoxy-3,4-dimethoxybenzyl)-thiophene are obtained.

IR$\nu_{Max}^{Nujol}$ (cm$^{-1}$): 3100, 1595, 1510

(2) 6.8 ml of 2.5M solution of n-butyl lithium in hexane are added dropwise under cooling to a tetrahydrofuran solution of 4.10 g of the product obtained in the paragraph (1). After stirring the mixture, 1.25 g of N,N-dimethylformamide are added thereto, and the mixture is stirred and then warmed up to room temperature. Water is added thereto, and the mixture is extracted with ethyl acetate. The extract is dried and evaporated under reduced pressure. The residue is purified by using silica gel column, whereby 3.81 g of 3-(methoxy-3,4-dimethoxybenzyl)-2-thiophenecarboaldehyde are obtained.

IR$\nu_{Max}^{Nujol}$ (cm$^{-1}$): 1660

What we claim is:

1. A biphenyl derivative of the formula:

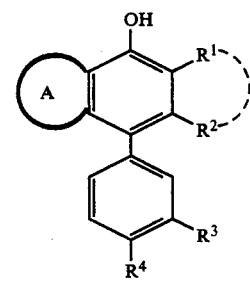

wherein each of R$^1$ and R$^2$ is a lower alkoxycarbonyl group, or R$^1$ and R$^2$ are combined together to form a group of the formula:

each of R$^3$ and R$^4$ is a lower alkoxy group; and Ring A is a thiophene ring, or a salt thereof.

2. The compound according to claim 1, wherein each of R$^1$ and R$^2$ is an alkoxycarbonyl group of 2–5 carbon atoms, or R$^1$ and R$^2$ are combined together to form a group of the formula:

and each of R$^3$ and R$^4$ is an alkoxy group of 1–4 carbon atom(s).

3. The biphenyl derivative compound 4-hydroxy-5,6-bis-(methoxycarbonyl)-7-(3,4-dimethoxyphenyl)benzo[b]thiophene or a salt thereof.

4. The biphenyl derivative compound 4-hydroxy-5-hydroxymethyl-7-(3,4-dimethoxyphenyl)benzo[b]thiophene-6-carboxylic acid lactone or a salt thereof.

5. A pharmaceutical composition having hypolipidemic activity, which comprises a therapeutically effective amount of a biphenyl derivative of the formula:

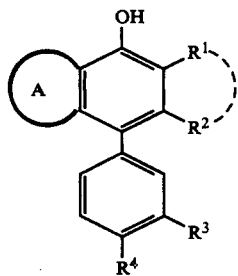

wherein each of $R^1$ and $R^2$ is a lower alkoxycarbonyl group, or $R^1$ and $R^2$ are combined together to form a group of the formula:

each of $R^3$ and $R^4$ is a lower alkoxy group; and Ring A is a thiophene ring, or a salt thereof.

6. The pharmaceutical composition according to claim 5, for use in the treatment or prophylaxis of hyperlipidemia or arteriosclerosis.

7. A method for therapeutic treatment of prophylaxis of hyperlipidemia which comprises administering to a warm-blooded animal a therapeutically effective amount of a biphenyl derivative of the formula:

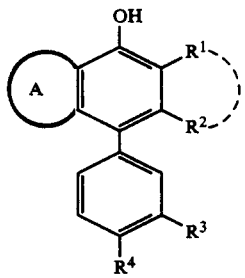

wherein each of $R^1$ and $R^2$ is a lower alkoxycarbonyl group, or $R^1$ and $R^2$ are combined together to form a group of the formula:

each of $R^3$ and $R^4$ is a lower alkoxy group; and Ring A is a thiophene ring, or a salt thereof.

* * * * *